United States Patent [19]

Bartels-Keith et al.

[11] 4,371,603
[45] Feb. 1, 1983

[54] AMINO HYDROXY CYCLOHEXENONE DEVELOPING AGENTS

[75] Inventors: James R. Bartels-Keith, Lexington; Eva R. Karger, Arlington, both of Mass.

[73] Assignee: Polaroid Corporation, Cambridge, Mass.

[21] Appl. No.: 221,291

[22] Filed: Dec. 30, 1980

[51] Int. Cl.³ .......................... G03C 1/42; G03C 1/48
[52] U.S. Cl. ................................. 430/218; 430/239; 430/249; 430/380; 430/390; 430/405; 430/442; 430/484; 430/543; 430/559; 430/566
[58] Field of Search ............... 430/366, 559, 543, 218, 430/442, 484, 405, 380, 390, 239, 249

[56] References Cited

U.S. PATENT DOCUMENTS 3,690,872  9/1972  Gabrielsen et al. ................. 430/234
3,700,442 10/1972  Gabrielsen et al. ................. 430/234
3,816,137  6/1974  Gabrielsen et al. ................. 430/203

*Primary Examiner*—John E. Kittle
*Assistant Examiner*—John L. Goodrow
*Attorney, Agent, or Firm*—Sybil A. Campbell

[57] ABSTRACT

This invention relates to amino hydroxy cyclohexenones of the formula

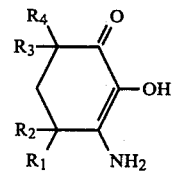

wherein $R_1$, $R_2$, $R_3$ and $R_4$ each are alkyl, usually containing 1 to 20 carbon atoms.

In another embodiment, the present invention is directed to the use of the above-denoted compounds as photographic silver halide developing agents and to photographic processes, products and compositions employing the same.

18 Claims, No Drawings

AMINO HYDROXY CYCLOHEXENONE DEVELOPING AGENTS

BACKGROUND OF THE INVENTION

1. Field of the Invention

This invention relates to novel chemical compounds and to their use as photographic silver halide developing agents.

2. Description of the Prior Art

A variety of reductone compounds including amino reductones are known, and a number of such compounds have been used as reagents in photography. For example, U.S. Pat. No. 3,690,872 is directed to the use of certain amino hydroxy cycloalkenones as silver halide developing agents including 3-amino-2-hydroxy-2-cyclopentenones and 3-amino-2-hydroxy-2-cyclohexenones substituted in the 4-position with alkyl containing 1 to 5 carbon atoms. As discussed in this patent at column 3, lines 14–75, the preparation of 2-hydroxy-3-morpholino-2-cyclohexenone is typical of the method of preparing the amino hydroxy cycloalkenone developing agents and comprises refluxing equimolar amounts of morpholine, 3-chloro-1,2-cyclohexanedione and triethylamine in anhydrous ethyl acetate under at atmosphere of nitrogen. U.S. Pat. No. 3,700,442 is directed to the use of esters of amino reductones, e.g., esters of amino hexose reductones as developing agent precursors. As discussed in this patent at column 3, lines 13–24, a typical method of preparing the described amino hexose reductones consists of heating a reducing sugar and an aliphatic or cyclic secondary amine in a substantially water free reaction medium in the presence of an acidic reductone-forming catalytic agent such as phosphoric acid.

The present invention is concerned with a new class of amino hydroxy reductones which also are useful as silver halide developing agents.

SUMMARY OF THE INVENTION

It is, therefore, one object of the present invention to provide novel chemical compounds.

Another object of the present invention is to provide photographic products, processes and compositions employing the subject compounds.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

DETAILED DESCRIPTION OF THE INVENTION

The novel compounds of the present invention may be represented by the formula

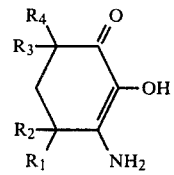

wherein $R_1$, $R_2$, $R_3$ and $R_4$ each are alkyl, usually containing 1 to 20 carbon atoms, for example, methyl, ethyl, nonadecyl, undecyl and dodecyl. These $R_1$, $R_2$, $R_3$ and $R_4$ groups may be the same or different and usually are the same. When employed as silver halide developing agents, it will be appreciated that such compounds include the salts thereof, e.g., the hydrochloride.

The subject compounds may be prepared by bromination of the selected 3,3,5,5-tetrasubstituted cyclohexanone to give the corresponding 2,6-dibromo compound followed by converting the brominated compound to the 2-hydroxy-4,4,6,6-tetrasubstituted cyclohex-2-enone using a Favorski-type rearrangement in potash, nitrating with nitric acid in acetic acid solution to give the 2-hydroxy-3-nitro-4,4,6,6-tetrasubstituted cyclohex-2-enone and reducing the nitro group to amino by hydrogenation using palladium-on-carbon catalyst. The aforementioned bromination and rearrangement steps have been described by C. Sandris and G. Ourisson, Bull. Soc. Chim. France, 1956, pp. 958–966.

The following Example illustrates the preparation of the compounds within the scope of this invention and is given for purposes of illustration only.

EXAMPLE

Preparation of the compound having the formula

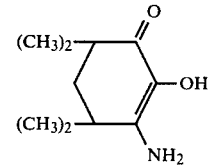

(1) 3,3,5,5 Tetramethyl cyclohexanone (50 g) was dissolved in 65 ml acetic acid and stirred mechanically in a 3 necked 500 ml round bottom flask equipped with dropping funnel and thermometer. The flask was placed in an ice bath and the solution cooled to 15°–20° C. Bromine was dissolved in 65 ml of acetic acid and this solution was added slowly ($\frac{1}{2}$–$\frac{3}{4}$ hours) so that the temperature never rose above 20° C. After about $\frac{2}{3}$ of the bromine solution had been added, the yellowish solution changed very quickly into a thick yellow paste. After all the bromine had been added, a small amount of acetic acid was added and the product was collected and sucked dry giving a white solid which was washed repeatedly with water and then air-dried overnight giving 97 g of solid. The solid was recrystallized from hot methanol (about 1400 ml) giving a white solid (51.5 g) melting range 173°–175° C. Evaporation of the mother liquors to about half volume gave a further 17 g of 2,6-dibromo-3,3,5,5-tetramethyl-cyclohexanone.

(2) To a stirred solution of potassium hydroxide (50 g) in 1500 ml of distilled water was added the brominated compound of step 1 (50 g). Stirring was continued for 24 hours. The solution was filtered to remove brominated compound which had not dissolved. The filtrate was cooled in an ice bath and concentrated sulphuric acid added dropwise until a white solid precipitated. The mixture was stirred for 30 minutes, after which the white solid was collected and recrystallized from a hot mixture of 200 ml of methanol and 100 ml of water, giving 2-hydroxy-4,4,6,6-tetramethylcyclohex-2-enone as white crystals, 13.5 g, melting range 85°–86° C.

(3) 2-Hydroxy-4,4,6,6-tetramethylcyclohex-2-enone (16.8 g) was dissolved in acetic acid and the solution warmed to 30° C. 70% $HNO_3$ (10 ml) was then added. No exotherm was observed. The reaction mixture was now warmed to 35° C. and acetic anhydride (11.3 ml) added dropwise (during 20–30 minutes) while maintaining the temperature between 35° and 40° C. After addition was complete stirring was continued for a further 15–30 minutes at 35° C. Distilled water (~500 ml) was then added until the reaction mixture became cloudy. Stirring was continued until crystallization occurred, more distilled water (about 1500 ml) was added and the mixture chilled overnight. 2-Hydroxy-3-nitro-4,4,6,6-tetramethylcyclohex-2-enone was collected as a pale yellow solid, 13.5 g (melting range 99°–105° C.).

(4) In a Parr bottle was placed 2-hydroxy-3-nitro-4,4,6,6-tetramethylcyclohex-2-enone (8.6 g), 250 ml of ethanol, and 10% Pd/C (1.5 g), and the mixture hydrogenated at 40 psi. Uptake was approximately 0.13 moles of hydrogen in 60–90 minutes. When no more hydrogen was taken up the catalyst was removed and the filtrate evaporated in a rotary evaporator at 35° C. giving a white solid with a yellow cast. Recrystallization from 80 ml of hot ethyl acetate (Norit) gave 4 g of white crystals, melting range 179°–181° C. Evaporation of the filtrate to about 30 ml gave further 2-hydroxy-3-amino-4,4,6,6-tetramethylcyclohex-2-enone product (0.7 g).

The hydrochloride salt of the hydroxy amino cyclohexenone compound was prepared as follows:

A suspension of 2-hydroxy-3-amino-4,4,6,6-tetramethylcyclohex-2-enone (4.6 g) in 50 ml of absolute methanol was cooled in an ice bath, and anhydrous hydrogen chloride bubbled into the mixture for 10 minutes. The cyclohexenone went into solution almost immediately after addition of HCl was begun. Anhydrous ether (about 1 liter) was then added. The white solid that precipitated was collected and washed with anhydrous ether, giving the corresponding hydrochloride salt (4.5 g), melting range 193°–197° C.

As indicated above, the subject compounds are useful as silver halide developing agents and are useful in conventional or "tray" development and also are useful in diffusion transfer processes for forming images in silver or in color. Such processes are now well known in the art; see, for example, U.S. Pat. Nos. 2,543,181; 2,647,056; 2,983,606; etc. In processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image.

In silver diffusion transfer processes, processing of the exposed silver halide emulsion is effected in the presence of a silver halide solvent, such as sodium thiosulfate, which forms a diffusible complex with the undeveloped silver halide. The soluble silver complex thus formed diffuses to the superposed image-receiving layer where the transferred silver ions are deposited as metallic silver to provide the silver transfer image. In preparing silver prints in this manner, the image-receiving element preferably includes a silver precipitating agent, for example, heavy metal sulfides and selenides as described in U.S. Pat. No. 2,698,237 of Edwin H. Land.

In color diffusion transfer processes, a photosensitive component comprising at least one photosensitive silver halide emulsion having a dye image-providing compound associated therewith in the same or in an adjacent layer is exposed to form a developable image then developed with a processing composition to form an imagewise distribution of a soluble and diffusible image-providing material which is transferred, at least in part, by diffusion, to a superposed image-receiving component comprising at least a dyeable stratum. These processes rely for color image formation upon a differential in mobility or solubility of dye image-providing material obtained as a function of development so as to provide an imagewise distribution of such material which is more diffusible and which, therefore, may be selectively transferred to the superposed dyeable stratum. The differential in mobility or solubility may be obtained, for example, by a chemical action such as a redox reaction, a silver ion-assisted cleavage reaction or a coupling reaction.

The dye image-providing materials which may be employed in such processes generally may be characterized as either (1) initially soluble or diffusible in the processing composition but which are selectively rendered non-diffusible in an imagewise pattern as a function of development; or (2) initially insoluble or non-diffusible in the processing composition but which are selectively rendered diffusible in an imagewise pattern as a function of development. These materials may be complete dyes or dye intermediates, e.g., color couplers.

Examples of initially soluble or diffusible materials and their use in color diffusion transfer processes are disclosed, for example, in U.S. Pat. Nos. 2,774,668; 2,968,554; 2,983,606; 3,087,817; 3,185,567; 3,230,082; 3,345,163 and 3,443,943. Examples of initially non-diffusible materials and their use in color transfer systems are disclosed in U.S. Pat. Nos. 3,443,939; 3,443,940; 3,227,550; 3,227,551; 3,227,552; 3,227,554, 3,243,294; 3,445,228; 3,719,488, 3,719,489 and 4,076,529.

In any of these systems, multicolor images may be obtained by employing a photosensitive element containing at least two selectively sensitized silver halide layers each having associated therewith a dye image-providing material exhibiting the desired spectral absorption characteristics. The most commonly employed elements of this type are the so-called tripack structures employing a blue-, a green- and a red-sensitive silver halide layer having associated therewith, respectively, a yellow, a magenta and a cyan image-providing material.

The photosensitive and image-receiving elements may be separate components which are brought together during processing and thereafter retained together as the final print or separated following image formation; or they may together comprise a unitary structure, e.g., an integral negative-positive film structure wherein the negative and positive, i.e., the photosensitive element and image-receiving element are laminated and/or otherwise physically retained together at least prior to image formation. Integral negative-positive film structures adapted for forming color transfer images visible without separation, i.e., wherein the image-receiving element containing the dye transfer image need not be separated from the photosensitive element for viewing purposes are described and claimed in U.S. Pat. Nos. 3,415,644; 3,415,645; 3,415,646; 3,573,043 and 3,573,044 in the name of Edwin H. Land and in U.S. Pat. Nos. 3,594,164 and 3,594,165 in the name of Howard G. Rogers.

In conventional development and in diffusion transfer photographic processes, the subject compounds may be used as the sole silver halide developing agent, or they may be employed in combination with another silver halide developing agent as an auxiliary developer or as the main component of the developing combination. Examples of developing agents that may be used in combination with the subject compounds include hydroquinone and substituted hydroquinones, such as, tertiary butyl hydroquinone, 2,5-dimethyl hydroquinone, methoxyhydroquinone, ethoxyhydroquinone, chlorohydroquinone; pyrogallol and catechols, such as, catechol, 4-phenyl catechol and tertiary butyl catechol; aminophenols, such as, 2,4,6-triaminophenol, 2,4-diaminophenol dihydrochloride and 4,6-amino-ortho-cresol; 1,4-diaminobenzenes, such as, p-phenylenediamine, 1,2,4-triaminobenzene and 4-amino-2-methyl-N,N-diethylaniline; ascorbic acid and its derivatives, such as, ascorbic acid, isoascorbic acid and 5,6-isopropylidine ascorbic acid; and hydroxylamines, such as N,N-di(2-ethoxyethyl)hydroxylamine and N,N-di(2-methoxyethoxyethyl)hydroxylamine.

When the compounds of the present invention are used in diffusion transfer processes, the processing composition if it is to be applied to the emulsion by being spread thereon in a thin layer usually includes a film-forming thickening agent. The processing composition may comprise, for example, one or more developing agents of the present invention and optionally, one or more conventional developing agents such as those enumerated above, an alkali such as sodium hydroxide or potassium hydroxide and a film-forming thickening agent such as a high molecular weight polymer, e.g., sodium carboxymethyl cellulose or hydroxy ethyl cellulose. As noted above, in the production of silver transfer images, a silver halide solvent is employed which may be included in the processing composition, or if desired, a silver halide solvent precursor such as those disclosed in U.S. Pat. No. 3,698,898 of J. Michael Grasshoff and Lloyd D. Taylor may be disposed in a layer of the film unit. In addition to the above ingredients, the processing composition may be further modified by the inclusion of restrainers, preservatives and other components commonly employed in developer compositions. All these materials are preferably in aqueous solution.

Rather than being dissolved in the aqueous alkaline processing composition prior to application thereof to an exposed silver halide emulsion, the developing agents of the present invention may be disposed prior to exposure in the photosensitive element, e.g., by placing them in, on or behind a silver halide emulsion layer. In this instance, the processing composition containing the developing agent is formed by application to the photosensitive element of an aqueous alkaline solution capable of solubilizing the developing agent.

Because they do not give rise to oxidation products that stain the image, the developing agents of the present invention are especially useful in photographic processes wherein it is desired to eliminate or minimize the need for washing and stabilizing operations subsequent to the formation of the positive image, e.g., to eliminate the need for print coating silver transfer images. Since their oxidation products are non-staining, the subject developing agents also find utility in diffusion transfer processes adapted to provide positive silver transfer images which may be viewed as positive transparencies without being separated from the developed negative silver image including such processes adapted for use in forming additive color projection positive images. Diffusion transfer processes of this type are described in U.S. Pat. Nos. 3,536,488 of Edwin H. Land and 3,615,428 of Lucretia J. Weed and in U.S. application Ser. No. 383,196 of Edwin H. Land filed July 27, 1973, now U.S. Pat. No. 3,894,871.

To illustrate the utility of the subject compounds as developing agents, a photosensitive element using, as the yellow dye,

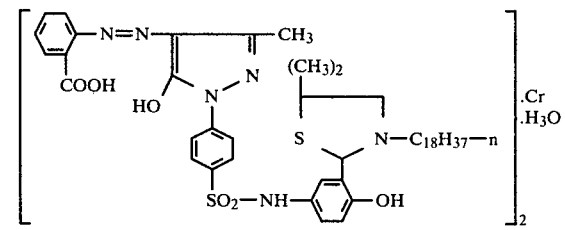

was prepared by coating a gelatin-subcoated 4 mil polyethylene terephthalate film base with the following layers:

1. a layer of yellow dye dispersed in gelatin and coated at a coverage of about 83 mgs./ft.$^2$ of dye and about 83 mgs./ft.$^2$ of gelatin;

2. a gelatino silver bromide emulsion coated at a coverage of about 40 mgs./ft.$^2$ of silver and about 60 mgs./ft.$^2$ of gelatin; and 3. a layer of gelatin coated at a coverage of about 30 mgs./ft.$^2$ of gelatin.

A transparent 4 mil polyethylene terephthalate film base was coated, in succession, with the following layers to form an image-receiving component:

1. as a polymeric acid layer, the partial butyl ester of polyethylene/maleic anhydride copolymer at a coverage of about 2,500 mgs./ft.$^2$;

2. a timing layer containing about a 40:1 ratio of a 60-30-4-6 copolymer of butylacrylate, diacetone acrylamide, styrene and methacrylic acid and polyacrylamide at a coverage of about 500 mgs./ft.$^2$; and 3. a polymeric image-receiving layer containing a 2:1 mixture, by weight, of polyvinyl alcohol and poly-4-vinylpyridine, at a coverage of about 300 mgs./ft.$^2$. The photosensitive element was exposed to a stepwedge, superposed with the image-receiving component and a layer of an aqueous alkaline processing composition was distributed by passing the sandwich between a pair of pressure-applying rollers in the dark.

The aqueous alkaline processing composition comprised:

| | |
|---|---|
| Water | 100 cc. |
| Sodium hydroxide | 7.5 g. |
| Carboxymethyl hydroxyethyl cellulose | ~3.0 g. |
| 6-methylthiomethyl-2,4-dihydroxypyrimidine | 1.5 g. |
| Sodium sulfite | 1.0 g. |
| Titanium dioxide | ~50.0 g. |

| -continued | |
|---|---|
| Compound of Example as HCl salt | 3.8 g. |

The resulting laminate was maintained intact to provide a color reflection print, and after about 10 minutes in the dark, the maximum and minimum reflection densities were measured for the positive yellow image. The maximum reflection density obtained was 1.79 and the minimum reflection density was 0.14.

It will be apparent that the relative proportions of the subject developing agents and of the other ingredients of the processing compositions may be varied to suit the requirements of a given photographic system. Also, it is within the scope of this invention to modify the formulations set forth above by the substitution of alkalies, silver solvents and so forth other than those specifically mentioned. Where desirable, it is also contemplated to include in the developer composition, other components as commonly used in the photographic art.

Since certain changes may be made in the herein defined subject matter without departing from the scope of the invention herein involved, it is intended that all matter contained in the above description should be interpreted as illustrative and not in a limiting sense.

What is claimed is:

1. A photographic product comprising a support, a silver halide emulsion carried on said support and a developing agent of the formula

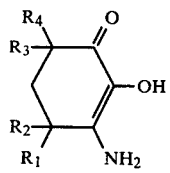

wherein $R_1$, $R_2$, $R_3$ and $R_4$ each are alkyl, said developing agent being carried in a layer on the same side of the support as said emulsion.

2. A product as defined in claim 1 wherein said $R_1$, $R_2$, $R_3$ and $R_4$ are the same.

3. A product as defined in claim 2 wherein said $R_1$, $R_2$, $R_3$ and $R_4$ each are methyl.

4. A product as defined in claim 1 which additionally includes a dye image-providing material associated with said silver halide emulsion.

5. A product as defined in claim 4 which includes a dyeable stratum in superposed relationship with said silver halide emulsion.

6. A method of developing a silver halide emulsion which comprises treating an exposed silver halide emulsion layer with an aqueous alkaline processing composition of a silver halide developing agent of the formula

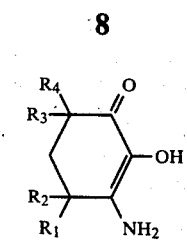

wherein $R_1$, $R_2$, $R_3$ and $R_4$ each are alkyl.

7. A method as defined in claim 6 wherein said silver halide developing agent is in a layer of a photosensitive element including said silver halide emulsion, and said solution of said developing agent is formed by applying to said photosensitive element a solution of aqueous alkali in which said developing agent is soluble.

8. A method as defined in claim 6 wherein said $R_1$, $R_2$, $R_3$ and $R_4$ are the same.

9. A method as defined in claim 8 wherein said $R_1$, $R_2$, $R_3$ and $R_4$ each are methyl.

10. A method as defined in claim 6 wherein a dye image-providing material is associated with said silver halide emulsion.

11. A method as defined in claim 10 including the step of transferring an imagewise distribution of diffusible dye image-providing material to a superposed dyeable stratum to form a dye transfer image.

12. A method as defined in claim 6 wherein said processing composition includes a silver halide solvent and said silver halide emulsion is developed in the presence of an image-receiving material superposed on said emulsion to form a silver transfer image on said image-receiving material.

13. A method as defined in claim 12 wherein said processing composition additionally includes a film-forming thickening agent.

14. A photographic developer composition comprising an aqueous alkaline solution containing a silver halide developing agent of the formula

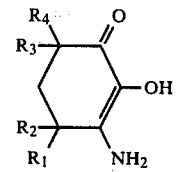

wherein $R_1$, $R_2$, $R_3$ and $R_4$ each are alkyl.

15. A developer composition as defined in claim 14 wherein said $R_1$, $R_2$, $R_3$ and $R_4$ are the same.

16. A developer composition as defined in claim 15 wherein said $R_1$, $R_2$, $R_3$ and $R_4$ each are methyl.

17. A developer composition as defined in claim 14 which includes a silver halide solvent.

18. A developer composition as defined in claim 17 which additionally includes a film-forming thickening agent.

* * * * *